United States Patent
Cerofolini

(10) Patent No.: US 6,572,548 B2
(45) Date of Patent: Jun. 3, 2003

(54) METHOD AND APPARATUS FOR ULTRASOUND IMAGING, PARTICULARLY FOR THREE-DIMENSIONAL IMAGING

(75) Inventor: Marino Cerofolini, Arezzo (IT)

(73) Assignee: Esaote, S.p.A., Casale Monferrato (IT)

( * ) Notice: Subject to any disclaimer, the term of this patent is extended or adjusted under 35 U.S.C. 154(b) by 0 days.

(21) Appl. No.: 09/882,598

(22) Filed: Jun. 15, 2001

(65) Prior Publication Data

US 2002/0016546 A1 Feb. 7, 2002

(30) Foreign Application Priority Data

Jun. 22, 2000 (IT) .................................. SV2000A000027

(51) Int. Cl.$^7$ ................................................ A61B 8/00
(52) U.S. Cl. ........................ 600/443; 600/458; 128/916
(58) Field of Search ..................... 600/437, 440–447, 600/459–467, 407, 424–435, 449–458; 601/2, 84, 89, 93; 73/625, 626, 633, 624; 367/7, 11, 138; 128/916; 424/9.52; 29/25.35

(56) References Cited

U.S. PATENT DOCUMENTS

| | | | |
|---|---|---|---|
| 5,070,879 A | * 12/1991 | Herres | 600/444 |
| 5,159,931 A | 11/1992 | Pini | 128/660.07 |
| 5,226,113 A | 7/1993 | Cline et al. | 395/124 |
| 5,396,890 A | 3/1995 | Weng | 128/660.07 |
| 5,487,338 A | 1/1996 | Lewis et al. | 101/154 |
| 5,497,776 A | 3/1996 | Yamazaki et al. | 128/660.09 |
| 5,740,804 A | 4/1998 | Cerofolini | 128/660.1 |
| 5,899,861 A | 5/1999 | Friemel et al. | 600/443 |
| 5,928,151 A | 7/1999 | Hossack et al. | 600/443 |
| 6,036,646 A | 3/2000 | Barthe et al. | 600/459 |
| 6,059,728 A | 5/2000 | Ritter | 600/443 |
| 6,276,211 B1 | 8/2001 | Smith | 73/626 |

FOREIGN PATENT DOCUMENTS

| | | | |
|---|---|---|---|
| EP | 952463 | 10/1999 | G01S/15/89 |
| FR | 2651990 | 3/1991 | A61B/8/14 |
| WO | 98/43109 | 10/1998 | |

* cited by examiner

Primary Examiner—Marvin M. Lateef
Assistant Examiner—Ali M. Imam
(74) Attorney, Agent, or Firm—Woodard, Emhardt, Naughton Moriarty & McNett LLP

(57) ABSTRACT

A method of ultrasound imaging, including the following steps, transmitting ultrasonic beams generated by transducers (20) into an object volume (v) such as an object body or a part thereof, receiving (20) and storing (3) signals reflected from said object volume, processing and receiving signals into image data associated to image dots or lines of a video display (8), and displaying at least a few image data on the display (8) in accordance with parameters set by a user and related to a predetermined section or projection plane of the image of said object volume. According to the invention, scanning is only performed in the region of the object body which coincides with the section plane or the image projection plane (P) of the object volume along which imaging is to be performed.

38 Claims, 11 Drawing Sheets

Fig. 1D   Fig. 1E

METHOD AND APPARATUS FOR ULTRASOUND IMAGING, PARTICULARLY FOR THREE-DIMENSIONAL IMAGING

REFERENCE TO RELATED APPLICATION

The present patent application claims foreign priority benefits under 35 U.S.C. §119 to Italian patent application No. SV2000A000027, filed Jun. 22, 2000, now pending.

BACKGROUND OF THE INVENTION

The invention relates to a method of ultrasound imaging, including the following steps:

- transmitting ultrasonic beams generated by transducers into an object volume corresponding to an object body or a part thereof;
- receiving and storing echo signals generated by the ultrasonic beams in said object volume;
- processing the received signals into image data associated to image dots or lines of a video display;
- displaying at least a few image data on the display in accordance with parameters set by the user and related to a predetermined section or projection plane of the image of said object volume;
- processing of ultrasonic beams and/or displaying being specifically predetermined with reference to a preliminary selection of a section plane or an image projection plane of the object volume to be imaged.

Methods of this type are known, for instance, from U.S. Pat. No. 5,396,890 or EP 952,463 or U.S. Pat. No. 5,226,113, U.S. Pat. No. 5,928,151 and U.S. Pat. No. 5,497,776.

These known methods aim at performing three-dimensional ultrasound imaging by a number of different techniques, e.g. acquiring a succession of section planes of the object body, processing the individual reflected echoes in each plane and constructing a three-dimensional image memory in which the received echo signals are associated to a set of voxels, i.e. image dots of a three-dimensional image, while accounting for the relative position of the individual scan planes.

During image acquisition, the whole object volume is generally scanned, through successive two-dimensional section planes staggered to a predetermined extent to cover the whole object volume. Then, the signals of the reflected echoes are processed and transformed into image data in the form of a three-dimensional matrix of image dots. This process must be substantially exhaustive to allow the desired image to be displayed in a plane having any spatial orientation and crossing the object volume. Hence, a selected image may be displayed only after scanning the whole volume and, above all, after completely processing the echo signals to generate the three-dimensional image data matrices. Therefore, image displaying times are relatively long and require highly powerful and costly hardware to obtain an acceptable processing time. Moreover, these very long displaying times are a severe shortcoming when related to the difficulties the patient encounters in keeping perfectly still for long periods of time and when transient events are to be observed whose starting time is not exactly predefined. An important example consists in the combined use of ultrasound imaging with the so-called contrast agents. These substances are injected into the tissues under examination. A certain time, of a few tens of seconds, passes before they reach the object region. Further, the time during which contrast agents remain in the object tissues, as regards both their passage therethrough and their decay, is short, also being of the order of a few tens of seconds. Hence, by using prior art imaging methods, it may be frequent that scanning is performed when contrast agents have not reached the object region yet. If this is the case, the doctor or the user will only be able to assess this condition later, when processing is completed, hence in unfavorable conditions, and will not have the time for a new image acquisition in order that imaging may take place when contrast agents are present or have not decayed in the object region. In this case, a new injection of contrast agents will be required to repeat scanning. Such a situation is definitely undesirable, as it reduces the non-invasiveness degree of the ultrasound imaging method.

Identical or similar problems are encountered when the probe is not properly positioned, whereby even though scanning is performed while contrast agents are present in the object region, it must be repeated, for instance if probe orientation does not allow scanning of the volume of interest and provides an unusable or anyway useless image.

The multiple techniques described in the above documents are based on a concept shared by all ultrasound imaging methods or systems, i.e. that the user may first select an imaging type, related to an imaging mode, e.g. the so-called B-mode, Doppler, Power Doppler, harmonic imaging, etc.

The selection of the view or section plane of interest takes place after image acquisition and processing of image data matrices. These steps are substantially preset in the apparatus.

The invention has the object of providing an ultrasound imaging method, particularly in three dimensions, which allows to obviate the drawbacks of prior art methods, without requiring any considerable complication of the method and higher costs of the apparatus for implementing it, while allowing a real time image display in section or projection planes having any orientation in space and with reference to the volume of interest.

The invention achieves the above purposes by providing a method of ultrasound imaging as described above, which has the following additional steps:

- defining a virtual volume coincident with the object body or part thereof or a three-dimensional reference system, provided it has a definite orientation with respect to the imaging planes generated by the ultrasound probe;
- selecting the section plane of the object body and/or part thereof along which ultrasound imaging is to be performed.
- determining the position-defining coordinates for the dots which form said section plane along which imaging is to be performed, with reference to the virtual volume;
- restricting the scanning operation to the region which coincides with said section plane along which imaging is to be performed;
- transmitting the transmission signals and receiving the reflected echoes only along such lines of view of the probe which coincide with the surface or the projection slice of the selected section plane along which imaging is to be performed;
- only processing and displaying the received echo signals.

This method drastically reduces the number of steps required for image data processing from the received signals and considerably speeds up such processing. In fact, thanks to the preliminary selection of the section plane of the object body or part thereof to be imaged, the method restricts not only the amount of signals to be processed for imaging, but also scanning times, with the probe transmitting and receiving not along the whole scan plane thereof, but only for a limited slice, coinciding with said projection region of the selected section plane, along which imaging is to be performed.

It will be understood that the principle of this method is reversed as compared to the one currently in use. At present, as stated above, the modes of transmitting and receiving ultrasonic signals and processing reflected echoes are preset and independent from the section plane or projection plane of the object volume to be imaged and the selection of said planes, or more particularly of their orientation with respect to the object volume takes place a posteriori, i.e. when substantially all useful signals have been converted to image data by scan converters. In the present invention, it is the selection of the section plane or of the projection plane to be imaged which determines the modes of transmitting and receiving ultrasonic signals, as well as processing modes, aimed at generating the image data three-dimensional matrix, wherefrom images are generated. From said transmission and reception, i.e. from the scanning operation, all the regions which do not intersect or fall within the selected section plane along which imaging is to be performed, are excluded, to filter out all the signal portions which do not contribute to form dots, lines or unit volumes of the image coinciding with or belonging to the section plane to be imaged.

It is important to observe that the principle of the method of the invention may apply to any type of ultrasound imaging, for instance B-Mode, Doppler, Power Doppler, Harmonic Imaging, and even to combinations of said modes.

The above principle also applies to all types of probes.

Particularly, said principle is suitable for a real time display of so-called three-dimensional ultrasound images.

According to an improvement, it is possible to receive and store reflected echo signals even of regions which are not coincident with the selected section plane or with the selected projection plane to be imaged and to provide, simultaneously to or after image processing of signals coinciding with said planes, even processing of the remaining signals or signal portions into image data.

As a further improvement, there may be provided several modes of transmitting and receiving ultrasonic signals along the different scan lines which form each scan plane of the probe, depending on their being coincident with the section plane to be imaged or not coincident therewith. In fact, it is possible to perform scanning with non optimal parameters, hence in a shorter time, for the scan lines which do not coincide with the section plane along which imaging is to be performed, whereas parameters are optimized for the lines which coincide with the section plane along which imaging is to be performed. The regions which do not coincide with the section plane to be imaged may be also scanned along a reduced number of scan lines or by a reduced number of transducers, as compared with the number of lines or number of transducers activated in the regions of the scan plane of the probe which coincide with the section plane along which imaging is to be performed.

With particular reference to three-dimensional ultrasound imaging techniques, the invention provides the combination with a three-dimensional scanning method including the following steps:

performing a three-dimensional scan of the object volume, i.e. transmitting ultrasonic signals into the object body while focusing them along individual section planes having different orientations and positions and such that all the individual section planes together cover different and predetermined sections arranged over the extension of the whole object volume, or focused on individual adjacent unit volumes which cover, as a whole, all the object body, and receiving the corresponding reflected echoes, each section plane being formed by a series of parallel and adjacent section lines, or each section slice being formed by a plurality of unit scan volumes, which are formed, in turn, by a plurality of adjacent scan lines;

and processing the received echo signals into image data in relation to their position in space with reference to scan modes;

storing image data in a memory and transforming them into image dots or lines on a video display;

the method being further characterized by the following steps:

generating a virtual volume, containing or coinciding at least partly with the volume of the object body or part thereof or a three-dimensional reference system, provided it has a precise orientation with respect to the imaging planes generated by the ultrasound probe;

setting or selecting the orientation of a predetermined section plane of the object volume or of a predetermined projection plane of said object volume prior to the scanning, processing and displaying process;

determining the lines of said selected section or projection plane which intersect the individual scan planes and/or the unit volumes coinciding with said section or scan plane.

only transmitting ultrasonic signals and receiving echoes therefrom along said lines of said selected section or projection plane which intersect the individual scan planes and/or the unit volumes coinciding with said section or scan plane.

only processing into image data and into signals for controlling the video display such reflected signals or parts thereof which are related to said lines intersecting the selected section plane or projection plane to be displayed.

In accordance with an additional improvement, the method includes the following steps:

defining a virtual volume, which at least partially coincides with or encloses the object body or part thereof or a three-dimensional reference system, with respect to a first scan plane of the ultrasound probe.

selecting and setting position and orientation parameters of the section plane or of the projection plane to be imaged, relative to said virtual volume;

identifying the transmission signals and the corresponding echoes which relate to dots, unit volumes, lines or discrete bands or slices coincident or substantially coincident with said section plane or with said projection plane to be imaged by simply comparing the position references of the dots and/or lines contained in said section plane or in said projection plane to be imaged with the scan planes of the probe;

three-dimensionally scanning the object volume only in the region coinciding with the section plane along which imaging is to be performed, and storing the received echo signals and spatial position references univocally related thereto, with reference to individual discrete dots or unit volumes and/or to discrete scanning lines or bands or slices;

relating position and orientation parameters for the section plane or projection plane which has been predetermined for imaging with the references to the spatial position of each received signal;

only processing such received echo signals which relate to dots or lines coincident or substantially coincident with the dots or lines contained in the section plane or in the projection plane to be imaged.

Advantageously, it may be arranged that the transmitted signals are only focused in certain regions or along certain lines, with reference to the lines (L1, L2, L3, Ln) or volumes of each scan plane (S1, S2, S3, Sn) and/or scan unit volume respectively, which intersect said selected section plane (P) or projection plane.

When a mixed mode in used, in which the ultrasonic signals that do not coincide with the selected section plane along which imaging is to be performed are also transmitted and received with faster and less accurate techniques, then complete processing of reflected signals is possible, simultaneously with or after processing of the signals of each line intersecting each scan plane or scan volume, i.e. even signals from regions that do not coincide with said section plane along which imaging is performed may be processed, to generate image data for the whole volume of interest, having a lower accuracy, sharpness, definition, hence a lower quality, yet being useful to complete the image near the region of interest, which coincides with the section plane along which imaging has been performed.

In order to ensure a certain reliability, scanning tolerances may be set to provide that scanning is not only performed along lines or unit volumes coinciding with the section plane along which imaging is to be performed or with the projection thereof, but also, within predetermined limits, directly adjacent to said section plane or to the projection thereof.

Three-dimensional scan modes are well-known and are addressed by several published documents, such as, for instance the ones mentioned above. Particularly, there are scan modes which perform scans of the volume along an array of successive planes having such mutual positions and orientations as to cover a succession of sections arranged over the whole extension of the object volume.

To this end, it is possible to use common linear electronic or mechanical probes, or the so-called phased array probes, or probes whose transducers are arranged on a two-dimensional surface, the so-called 2D array probes.

The displacement of probes in the third dimension, i.e. in a direction substantially transverse to scan planes or scan volumes may occur in a manual, mechanical or motorized manner, by linear indexing or by oscillation or rotation. The relative position of the individual planes is determined by comparison to a reference plane, e.g. the plane of the first scan and through position sensors which detect the position and orientation of the probe or, in the case of motorized means, through predetermined steps of the probe from its starting position.

The advantages of the present invention are self-evident in the above description. With a probe for three-dimensional imaging having substantially constant optimized scanning times, by only scanning the lines or unit volumes substantially coinciding with the section plane along which imaging is to be performed and by only processing into image data the signals pertaining to said lines or unit volumes, imaging times are drastically reduced. Moreover, by providing a complete scan with a rougher process outside the region coincident with the section plane to be imaged, a panoramic image may be obtained, which contains low-definition, low-quality information of the regions around the section plane to be imaged and high-quality information along the selected section plane. It should be also noted that the method of the invention even allows to perform complete state-of-the-art three-dimensional scans with no construction change.

Fast processing to transform the received signals into an image of the selected section plane may allow to immediately assess if the conditions in which the volume of interest has been scanned are appropriate and to possibly perform new scans with no decay of the conditions desired for imaging.

This is particularly advantageous when contrast agents are used, as it allows to perform 3D scanning or imaging operations and to assess in real time if they were performed at the right time, i.e. when the object volume was reached by contrast agents.

If this is not the case, the immediate display of the desired image plane will allow to immediately perform a second scan without the long waiting times required by prior art methods, whereby said second additional scan will be certainly performed before contrast agents decay in their effect or leave the object volume.

Times are so fast that they allow to perform a succession of several scans before decay of contrast agents or departure thereof from the object volume. This is advantageous to assess the spread of the contrast agent in the object volume in relation to time.

To this end, the method may also include parallel or separate processing of the other received signals, unrelated to the scan lines which coincide with the section plane or projection plane selected for real time display.

The invention also relates to an ultrasound imaging apparatus, particularly for three-dimensional ultrasound imaging, including:

a probe having transducers for generating ultrasonic pulses and transducers for receiving said pulses;

a unit for controlling, generating and focusing said transmitted ultrasonic pulses in accordance with predefined scan modes;

a unit for reconstructing reflected echo signals with reference to focusing modes;

a unit for converting echo signals received and reconstructed into image data and a unit for storing said image data in which said image data are related to position parameters based on scan modes;

a unit for processing said image data into signals for controlling a displaying monitor;

a unit for setting spatial orientation parameters of the section and projection planes of the object volume along which imaging is to be performed;

a unit for controlling access to image data memories and processing of said data into control signals for the displaying monitor, based on the settings of spatial orientation parameters of section or projection planes of the object volume to be imaged;

the unit for controlling the scanning process and the unit for controlling access to image data memories and processing of said data into control signals for the displaying monitor being controlled based on the settings of spatial orientation parameters of section or projection planes of the object volume to be imaged for transmission and reception, as well as for processing and storage of such signals which only relate to dots, lines or unit volumes coinciding with said selected section or projection planes along which imaging is to be performed.

Particularly, the apparatus includes a main processor whereto the means for inputting the selected orientation of the plane to be imaged and the selected ultrasound imaging modes (B-mode, Doppler, Power Doppler, Harmonic Imaging, etc.) are associated, which controls a scan control processor whereto the scanning probe is connected, a processor for converting image data into monitor control signals and a storage control processor, whereto means for storage onto physical media are connected; a RAM unit whereto the positions of the individual scanning dots, planes or unit volumes are provided by the scan processor and whereto the storage control processor and the processor for converting scans into image data, as well as the displaying monitor, are connected.

Several types of probes may be used to implement the method and in combination with the above apparatus, and particular advantages are obtained with BISCAN probes, i.e. those performing two perpendicular scans, at least one of them being motorized. These probes may be of the sector— sector, linear-sector and phased array-sector type.

Nevertheless, other types of probes may be also used, such as those described in the following United States patents, each of which is hereby expressly incorporated by reference:

| U.S. Pat. No. | Issue Date | Inventor |
| --- | --- | --- |
| 5,899,861 | May 4, 1999 | Friemel, et al. |
| 6,036,646 | Mar. 14, 2000 | Barthe, et al. |
| 6,059,728 | May 9, 2000 | Ritter |
| 5,487,338 | Jan. 30, 1996 | Lewis, et al. |
| 5,159,931 | Nov. 3, 1992 | Pini |
| 5,740,804 | Apr. 21, 1998 | Cerofolini |

An accurate description of the scan modes of these probes is provided in U.S. Pat. No. 5,928,151, issued on Jul. 27, 1999 to Hossack, et al., and this description is to be intended as a part of the present description, since it embodies the state of the art and the modes for implementation of the method described above and claimed below, and is hereby expressly incorporated by reference.

Further improvements of the invention will form the subject of the subclaims.

The characteristics of the invention and the advantages derived therefrom will appear more clearly from the following description of a non limiting embodiment.

SUMMARY OF THE INVENTION

A method of ultrasound imaging according to one embodiment of the present invention comprises the steps of transmitting ultrasonic beams generated by transducers (20) into an object volume (v), receiving and storing signals generated by the ultrasonic beams in the object volume, processing the received signals into image data associated to image dots or lines of a video display, displaying at least a few image data on the display in accordance with parameters set by a user, processing of ultrasonic beams and/or displaying being specifically predetermined with reference to a preliminary selection of a section plane, characterized in that the method includes the additional steps of defining a virtual volume coincident with the object body, provided it has a definite orientation with respect to the imaging planes generated by the ultrasound probe, selecting the section plane of the object body along which ultrasound imaging is to be performed, determining the position-defining coordinates for the dots which form the section plane along which imaging is to be performed with reference to the virtual volume, restricting the scanning operation to the region which coincides with the section plane along which imaging is to be performed, transmitting the transmission signals and receiving the reflected echoes along such lines of view of the probe which coincide with the surface of the projection slice of the selected section plane, and only processing and displaying the received echo signals.

An ultrasound imaging apparatus for three-dimensional ultrasound imaging according to another embodiment of the present invention comprises a probe having transducers for generating ultrasonic pulses and receiving the ultrasonic pulses, a control unit for generating and focusing the transmitted ultrasonic pulses in accordance with predefined scan modes, a unit for reconstructing reflected echo signals with reference to focusing modes, a unit for converting echo signals received and reconstructed into image data, a unit for storing the image data in which the image data are related to position parameters based on scan modes, a unit for processing the image data into signals for controlling the displaying monitor, a unit for setting spatial orientation parameters of the section and projection planes of the object volume along which imaging is to be performed, a unit for controlling access to the image data memory and processing of the data into control signals for the displaying monitor based on the settings of spatial orientation parameters of section or projection planes of the object volume, and wherein the unit for controlling the scanning process and the unit for controlling access to the image data memory and processing of the data into control signals for the displaying monitor being controlled based on the settings of spatial orientation parameters of selection or projection planes of the object volume to the image for transmission or reception, as well as for processing and storage of such signals which only relate to dots, lines or unit volumes coinciding with the selected section or projection planes along which imaging is to be performed.

One object of the present invention is to provide and improved method of ultrasound imaging.

Another object of the present invention is to provide an improved ultrasound imaging apparatus for three-dimensional ultrasound imaging.

Related objects and advantages of the present invention will be apparent from the following description.

BRIEF DESCRIPTION OF THE DRAWINGS

FIGS. 1D to 1F are cross sectional views of FIGS. 1A to 1C.

DESCRIPTION OF THE PREFERRED EMBODIMENT

FIG. 1 shows in a very simplified manner the operation of the principle whereon the method of the invention is based, with reference to the use of a three-dimensional scanning probe of the swinging transducer type as shown in FIGS. 3 to 8. As will be apparent from the detailed description of said probes, the transducers thereof can provide scanning in a plane which contains the direction of propagation of the ultrasonic signals illuminating the object volume, i.e. the probe axis parallel to said propagation or shot direction and an axis perpendicular thereto and parallel to the transverse extension of the transducer array. The transducer array is swung about an axis parallel to said transverse axis (which also forms the second scanning dimension of the probe) by means of a motor and of an appropriate drive. The activation of the probe to transmit or receive is synchronized with the advance in such a manner as to cover the object volume V with a succession of scan planes having different predetermined orientations in space and a fanlike arrangement as illustrated and denoted as S1, S2, S3 and Sn in FIG. 1.

In prior art, all echo signals relating to the whole three-dimensional scan were collected, i.e. for each scan plane. These signals were processed to obtain from reflected echoes image data which, being univocally related to orientations or positions of planes with respect to a reference plane, were all processed before an image could be displayed. The operating personnel had the opportunity to indicate one or more section or projection planes having any spatial orientation, obviously related to the object volume. This selection was set in an image reconstructing processor which, based on position and orientation parameters of the selected plane/s to be displayed, selected data from the image data memory and generated the image. However, this process requires long processing times and when these times have to meet acceptable limits, they require the provision of powerful and relatively costly hardware. Nevertheless, prior art methods do not allow to obtain real images in real time, thereby causing the shortcomings discussed in the introduction of the present invention.

Figure 1A:
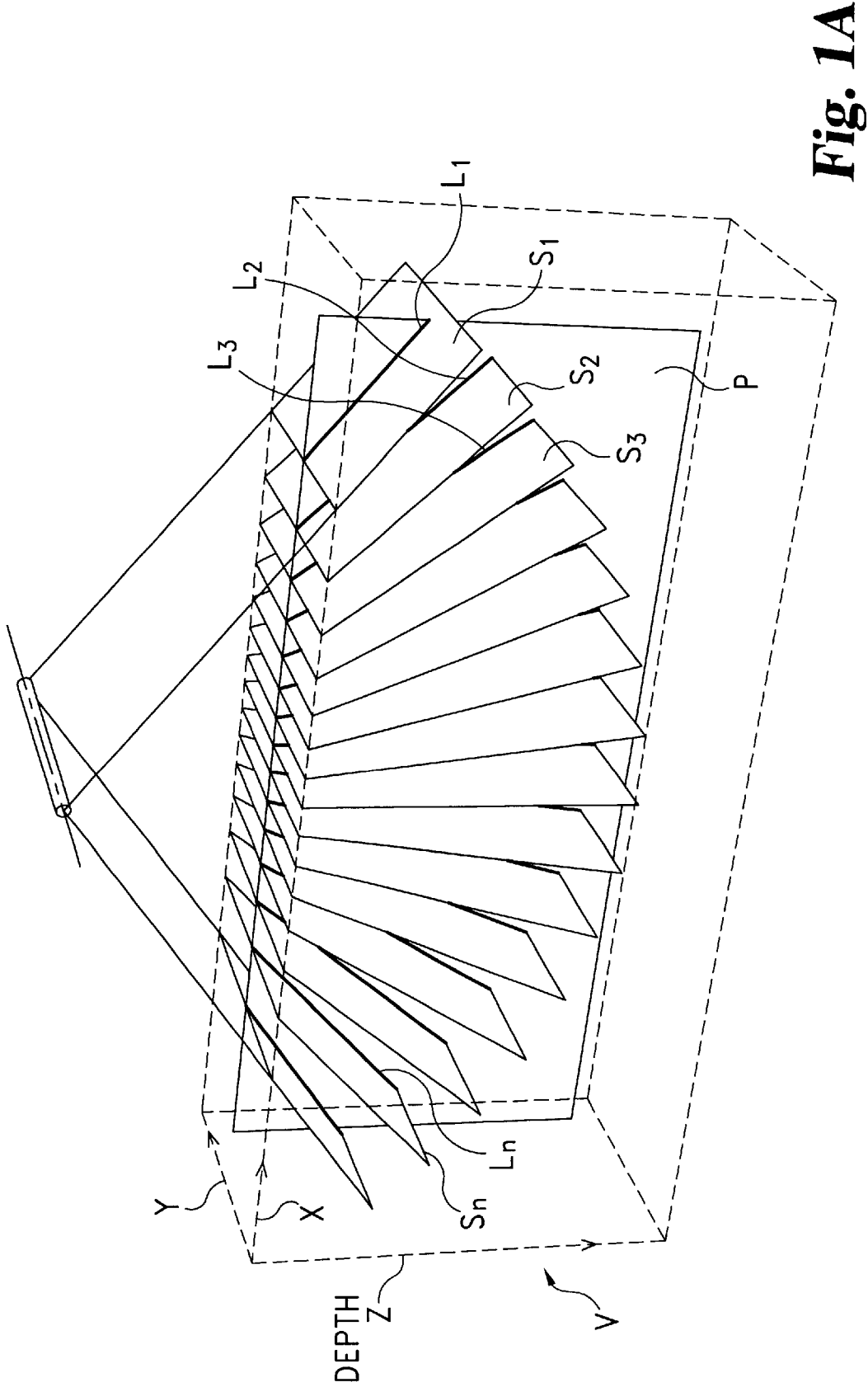
FIGS. 1A, 1B and 1C schematically show the principle of the method according to the present invention with reference to a swinging probe like any one of those shown in FIGS. 3 to 8, and with section planes along which imaging is performed, which have three different orientations.
Figure 1B:
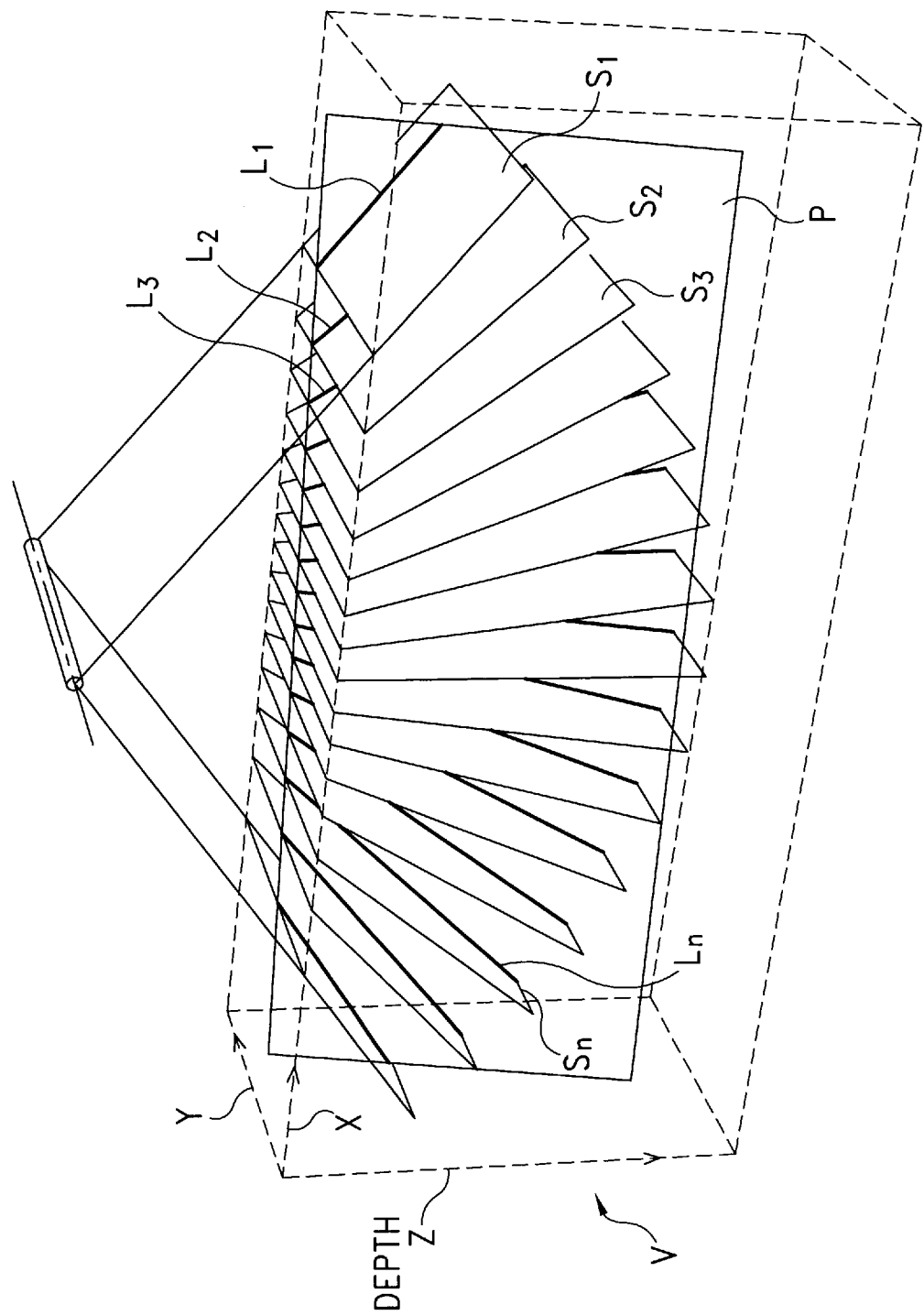
Figure 1C:
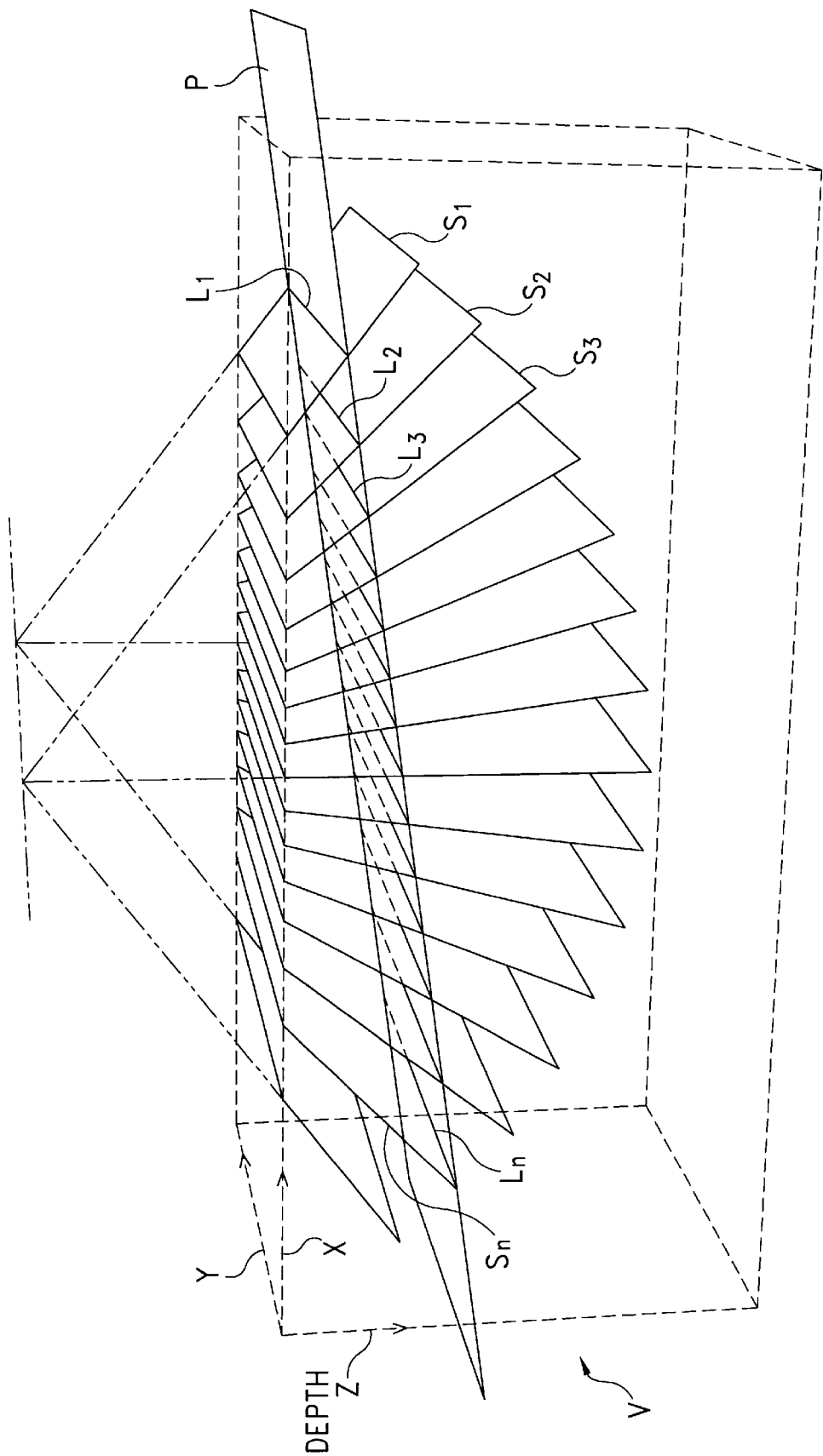

FIGS. 1A and 1C show the method of the invention in principle, which consists in setting, prior to scanning, the orientation and/or position parameters of the section or projection plane/s of the object volume to be displayed. With the positions of the scan planes S1, S2, S3, Sn being presumptively known, with respect to a reference scan plane for the probe, the method provides that scanning is only performed in each scan plane along the lines which form each scan plane and coincide with or intersect the lines L1, L2, L3, Ln, i.e. the lines of the selected imaging planes intersecting each scan plane S1, S2, S3, Sn. The positions of these lines in space can be presumptively determined by the main processor, based on the well-known relative position of the individual scan planes and on the user-preset orientation and position parameters of the planes to be displayed.

Therefore, in this case, scanning is not performed on the whole volume, whereby imaging times are drastically reduced and image processing is considerably speeded up, and imaging is actually performed in real time, thereby allowing the operating personnel to immediately make sure that scanning took place in the conditions required therefor.

Referring to the embodiments of FIGS. 1A and 1C, different planes P are shown which have different orientations. The most favorable situation is shown in FIG. 1A. In this Figure, the section plane P along which imaging is to be performed is perpendicular to the array of scan planes Sn of the probe. It is apparent that, in an ideal situation, scanning shall be performed along a single line for each plane, i.e. along the line coinciding with the lines Ln of the section plane P along which imaging is to be performed, which intersect the scan planes Sn of the probe. This is clearly shown in FIG. 1D in which the scan line is denoted as SCNL.

In FIG. 1B, the section plane P along which imaging is to be performed is inclined with respect to the scan lines forming each scan plane Sn of the probe. Hence, for each scan plane Sn, scanning is performed along all the scan lines which are coincident or intersect the corresponding intersection line Ln between the individual scan plane Sn of the probe and the section plane P along which imaging is to be performed. This is apparent in FIG. 1E, in which the two extreme scan lines SCNL(1) and SCNL(1+n) are shown.

FIG. 1C shows the most unfavorable condition, in which the section plane P along which imaging is to be performed fully cuts the scan planes Sn of the probe. In this condition, although scanning must be performed along all the lines of each scan plane, the invention allows to focus the transmitted signals on the intersection lines Ln between the section plane P along which imaging is performed and each scan plane, thereby achieving considerable quality results. This situation is also shown more clearly in FIG. 1F, in which the scan lines SCNL(1) and SCNL(1+m) are shown.

Since processing, as will be more apparent hereafter, is also only performed with reference to the data relating to the intersection lines Ln between the section plane P along which imaging is to be performed and the scan planes Sn of the probe, considerable reductions of imaging times are obtained.

Advantageously, the signals transmitted by the probe may be focused in a differentiated along the different scan lines which form the scan planes Sn even in the case of FIG. 1B. In fact, by presumptively knowing the orientation and length of the intersection lines Ln between the section plane P along which imaging is to be performed and the scan planes Sn of the probe, the focusing rule may be differentiated along the adjacent section lines, so that for each scan line of each scan plane Sn, the transmitted beam is focused on the point intersecting the corresponding line Ln.

Figure 1F:
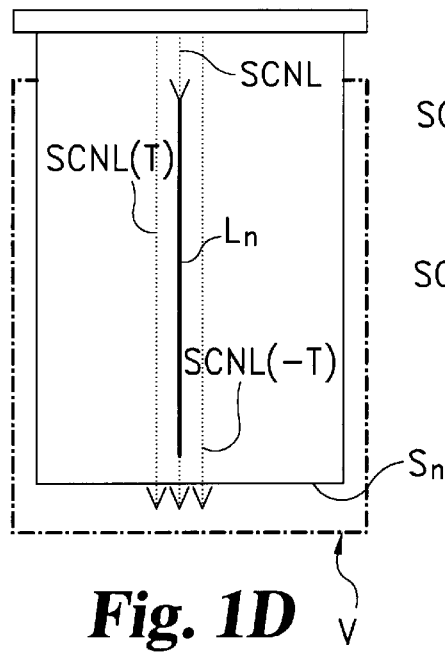
Figure 1F:
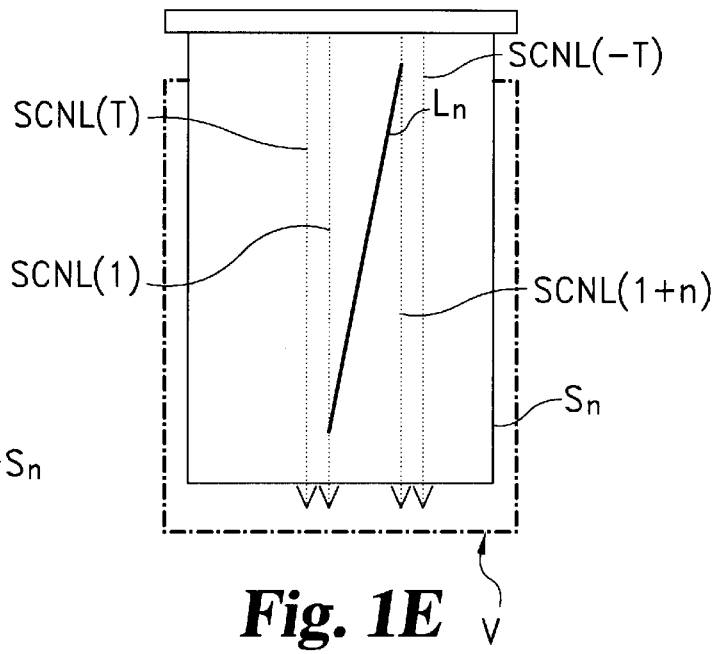
Figure 1F:
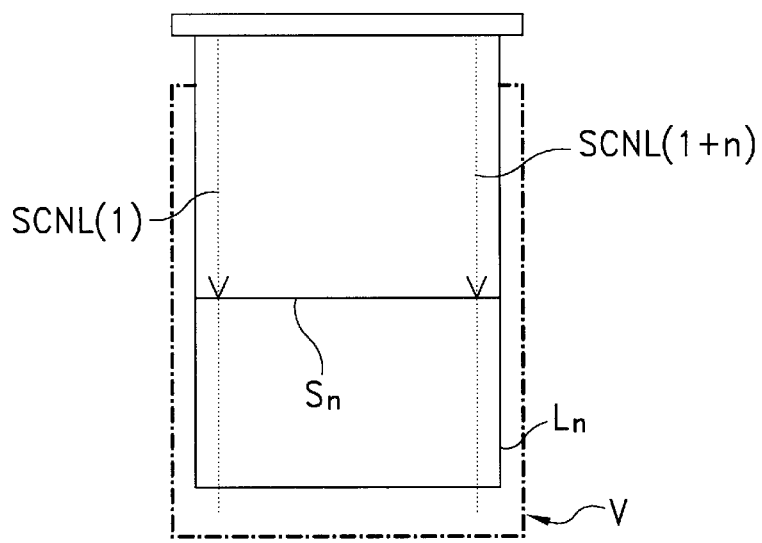

Obviously, in order to ensure imaging in any case, scanning may be performed for each scan plane Sn of the probe, even along lines directly adjacent to the scan lines intersecting the section plane P along which imaging is to be performed. This prevents any error caused by an imperfect correspondence between theoretical settings and the actual situation, e.g. errors and tolerances in the definition of univocal references between the actual position of the probe and the selected section plane along which imaging is to be performed. Anyway, the number of scan lines for each scan plane Sn of the probe is reduced. The above situation is shown in FIGS. 1D to 1F with the extreme and delimiting scan lines of the region scanned to ensure reliability being denoted s SCNL(T) and SCNL(-T).

It shall be noted that the above method may also apply to probes which have a two-dimensional transducer arrangement and hence do not scan planes, but slices having a predetermined volume and comprising several adjacent scan planes together. In this case, the concept of a scan line may be applied to a scan band or unit volume. In accordance with an additional improvement of the invention, when desired or compatible with the times required for the examination, the whole scan of each scan plane Sn of the probe may be performed, while limiting scan parameters for the lines which do not intersect or coincide with the section plane P along which imaging is to be performed, or possibly even the number of lines not intersecting said section plane P, to speed up both scanning and processing and storage to the detriment of quality, but anyway obtaining an image, even though of low quality, of the regions which do not coincide with the section plane P along which imaging is to be performed. These image data may be combined with high quality data processed along the section plane P. This may be of help when the selected section plane P, along which imaging is to be performed, does not coincide with the actually desired one, thereby allowing to verify that the slightly different settings of the orientation parameters for the section plane P provide the actually desired image.

This scanning method provides considerable advantages particularly when image scanning must be synchronized with transient events, specifically with the injection of contrast agents.

These contrast agents are used to display the behavior of flows, such as blood flow or else, and have specific ultrasound reflecting characteristics, to allow an optimal imaging of the flow which is naturally composed of particles having little echogenicity, or anyway a much lower echogenicity level than static tissues, which are typically hyperechogenic.

Contrast agents naturally take well-known times to reach the object volume, e.g. an organ or part thereof, of a human body or of any other animal or vegetal living creature. Moreover, contrast agents tend to leave rapidly the region of interest and/or to a rather fast decay.

Hence, the possibility of providing a three-dimensional complete scan of the object volume (which is typically relatively time-consuming for a single image display) in addition to the possibility of obtaining a real time image of the conditions of the object volume while the latter is scanned allows to promptly evaluate if scanning took place when contrast agents were present, or too early with respect to the passage thereof in the object volume and to perform a new scan, if needed, in time for synchronization with the passage of contrast agents.

Within the time range of contrast agent spread in the object volume, the method according to the invention also allows to perform several successive scans which provide information about perfusion of the flow through the object volume.

As a further improvement, even several parallel and adjacent section planes, covering a volumetric section slice, may be imaged. Imaging may be also performed on several spaced section planes P, which may be parallel and/or even transverse or intersecting each other.

It shall be noted that these possibilities do not require any change neither in the basic steps of the method of the invention nor of any apparatus used to implement the method.

It is apparent from the above disclosure that the method of the invention shall not be intended to be limited to the use in combination with the probes as shown in FIGS. 4 to 8, but may also apply to any type of probe or probe system being adapted to particularly perform a three-dimensional scan.

In accordance with an improvement of the method, since the spatial relation of the displaying plane to the scan planes depends on the relative position of the probe and the object volume, for example in the case of a combined use with contrast means, but without limitation thereto, it is possible to perform a first scan for setting the relative positions of the scan planes and the displaying plane, whereby position relations are defined more accurately. Imaging with contrast agents my be effected by performing a first scan without these agents and then, with the probe in position, by performing a continuous succession of scans while contrast agents are injected. Thanks to the possibility of always having a real time image displaying the conditions of the object volume, the operating personnel may decide to remove the unnecessary scans from the succession, for example those performed before contrast agents reach the object volume.

The present ultrasound imaging method is particularly effective and suitable for ultrasound imaging of the liver.

Figure 2:
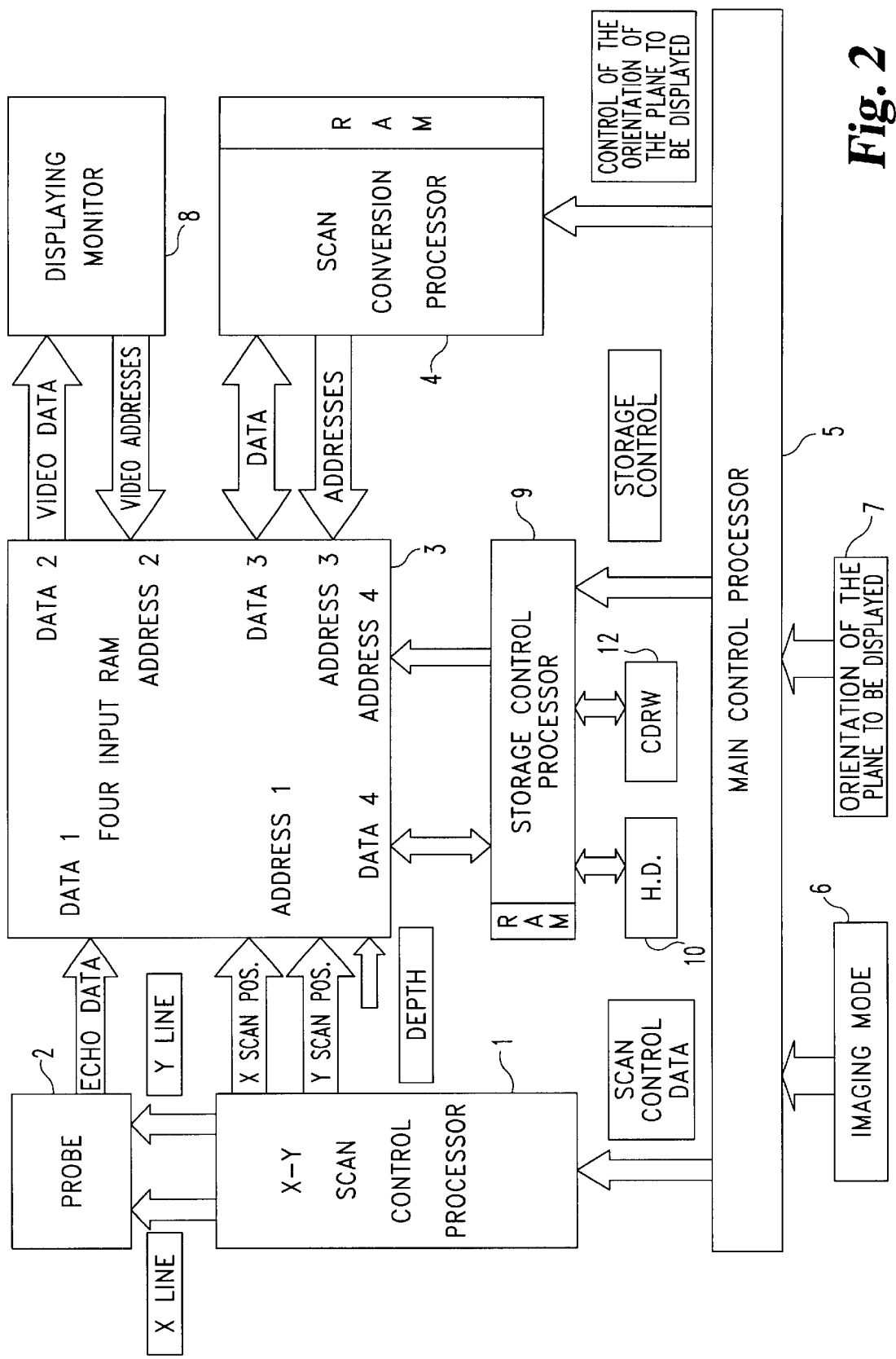
FIG. 2 is a block diagram of an apparatus for implementing the method of the invention.

FIG. 2 is a highly simplified block diagram of the construction of an ultrasound apparatus for implementing said method.

The apparatus has a scan control section, including a scan control processor 1 whereto a scanning probe 2 is connected, particularly a three-dimensional scanning probe and preferably a probe as shown in FIGS. 4 to 8.

In this case the processor controls the position of the transducers to univocally relate the received echoes with the scan plane and provides spatial position data to a four-input RAM unit, denoted as 3. Position parameters (here being referred to Cartesian coordinates but referable to any coordinate model for volume definition), form addresses 1, univocally related to the data address 1 of the RAM unit, whereto the probe supplies, after appropriate and usual processing, the data relating to the received echo signals. In this manner, the memory 3 becomes a three-dimensional memory in the form of a three-dimensional matrix in which the spaces of the image data memory are identified by an address corresponding or relating to the spatial location whereto image data are referred.

With particular reference to the illustrated embodiment, but with no limitation thereto as regards the implementability of the method and of the apparatus of the invention, scanning takes place through lines in two orthogonal directions denoted by lines x and y, whereas the third position coordinate is given by depth. The Cartesian system is shown in FIGS. 1A to 1C. Obviously, the scan planes as shown in FIGS. 1A to 1C in a fanlike arrangement are better described with reference to an angle. Anyway, the transformation of a system into another simply consists of a transformation between reference systems and is obtained by the application of a simple transformation formula. The third depth dimension may be detected and obtained based on reflection time. The RF signal received for each scan line has a time development and the portions arriving earlier relate to smaller depths as compared with the signal portions of the same scan line which arrive progressively later.

Obviously, echo signals are appropriately sampled on a predetermined time base to obtain discrete dots. Discretization obtained by sampling, i.e. sampling frequency affects the definition of the desired image.

The scan control processor is controlled by a main processor 5 which is connected to means 6 for setting the imaging mode or type, e.g. B-Mode, Doppler, Power Doppler or Harmonic Imaging, and to means 7 for setting orientation and/or position parameters of the section plane or of the projection plane to be displayed. Physically, these means may consist of handles, selectors, keyboards, etc., not shown in detail and possibly intended to load predetermined modes or orientation and position parameters.

The main processor 5 controls both the execution of imaging modes, thereby controlling the scan control processor 1, and a scan conversion processor, the so-called scan converter, which determines, based on the orientation and/or position parameters of the plane/s to be imaged, the lines L1, L2, L3, Ln of said planes to be imaged P intersecting the individual scan planes and identifies the memory addresses corresponding to image data along said intersecting lines, loads said data and transforms them into signals for controlling a monitor 8, by associating them to video addresses, at the inputs/outputs for addresses 3 and data 3 of the four input RAM unit 3. These data are read by the displaying monitor (data 2 and addresses 2 of the RAM unit 3) and are transformed into image lines, while the set of image lines forms the image relating to the section or projection plane to be displayed.

The data pertaining to the lines L1, L2, L3, Ln of said planes to be imaged P intersecting the individual scan planes Sn are also sent to the scan control processor, for determining the scan lines to be followed for each scan plane Sn.

The scan converter 4 is well-known and widely used in the art of ultrasound apparatuses and anyway is meant to process information with reference to a set of lines. Therefore, it might be a linear or two-dimensional scan converter.

The implementation of three-dimensional conversion, i.e. a conversion through imaging planes having any orientation in space, with respect to the object volume is achieved thanks to the combination of a linear or two-dimensional scan converter with the main processor, the scan control processor and the four input RAM unit, which allows to store and recall information collected upon scanning while constantly keeping it related to its proper position in space which is properly encoded by using data storage addresses. During processing, data are always univocally identifiable as regards their proper position in space and this ensures discrimination of the data pertaining to the lines of the displaying plane which intersect the scan planes for the purpose of reading them, processing them into display controls, and storing them in the form of image data in said memory, and finally recalling and displaying them on the monitor.

A storage control processor 9 is connected to the inputs/outputs of data 4 addresses 4 of the RAM unit 3 and controls, under the supervision of the main processor 5, the storage of data onto physical storage media, such as hard disks 10, floppy disks, CD rewritable 12.

As described above, the method of the invention is particularly effective with scanning probes of the three-dimensional motorized type, although it will be understood that the implementation of the method is not limited to the use of these probes.

The preferred design of these probes includes, according to a first embodiment, a transducer array 20 for performing a two-dimensional scan, i.e. a scan following a plurality of lines, named lines of view, or beams, named sector beams, oriented parallel or substantially parallel to the probe axis and arranged side-by-side to cover a whole predetermined section plane of the object volume.

The transducer array 20 is mounted inside a housing of a support 23 at an end of the probe. The support is mounted in such a manner as to swing about an axle 24 parallel to the extension of the scan planes. The swing axle 24 is provided at a certain distance from the transmission surface of the transducer array. The swinging support 23 has a toothed circular sector, i.e. a circular rack 25 on the side diametrically opposite to the axle 24, which circular rack 25 cooperates with a pinion 26. The pinion 26 is rotatably driven by a stepper motor 27 through a drive consisting of a gear 28 splined to the motor shaft and of a worm 29. The transducer array is outwardly covered by a cap 30 which is connected to the rest of the probe body, formed by a case for accommodating the connecting wires 31, the stepper motor and the drive with the pinion and the circular rack. The housing 32 for accommodating the transducer array, the support for the transducers and the circular rack, as well as the drive, is filled with an acoustic coupling liquid which is known and widely used in the art. The cap has sealing means, such as an o-ring 33, for contact with the rest of the probe body, and in the passage contained in the housing 32 for the stepper motor shaft and the connecting wires of the transducer array.

Figure 3:
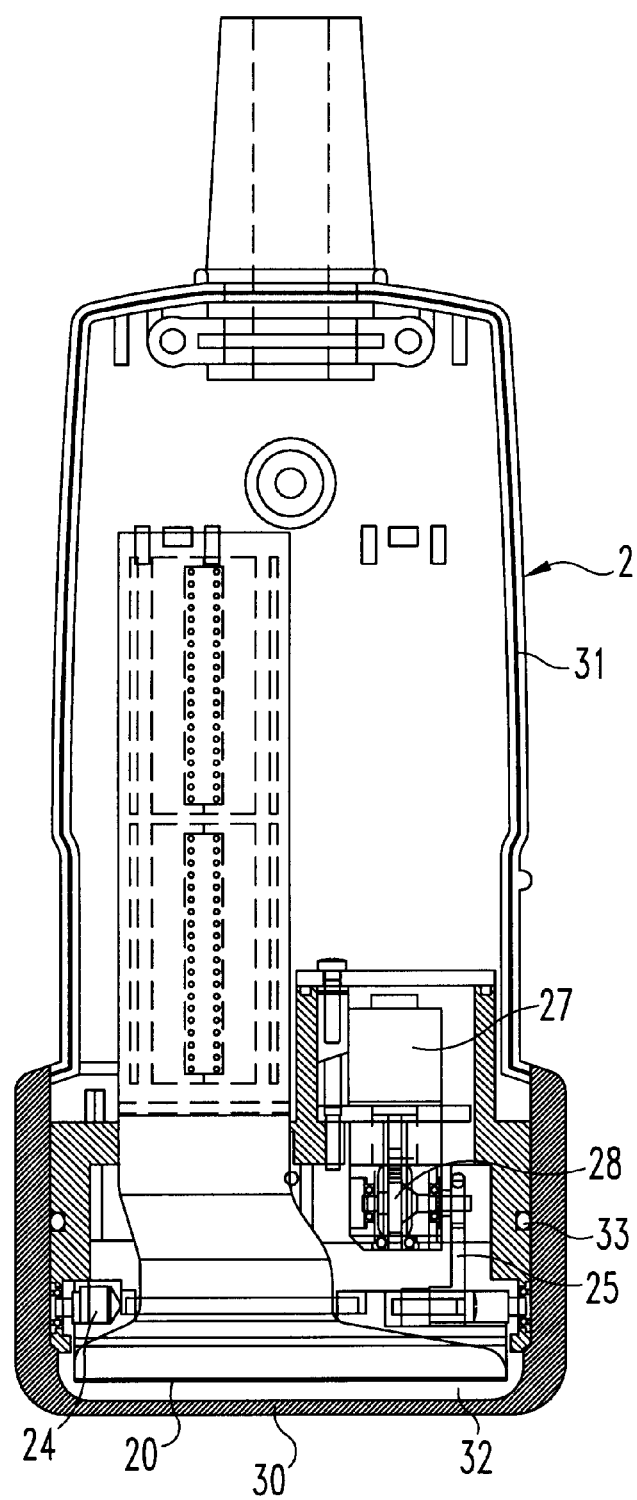
FIGS. 3 and 4 are two sectional views with respect to two different perpendicular planes of a first probe of the linear-sector type.
Figure 4:
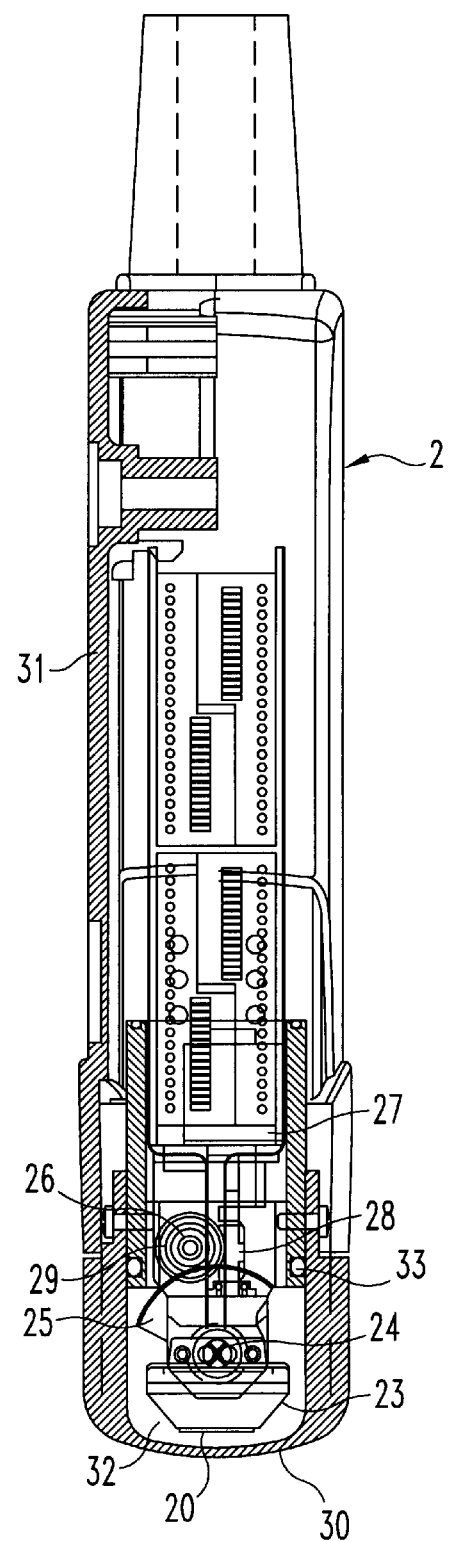

The probe as shown in FIGS. 3 and 4 is a so-called linear-sector probe. The transducers are arranged side-by-side along a line and are electronically activated by the control processor to generate an ultrasonic beam, whose focusing point is displaced, by appropriately activating the individual transducers arranged in a straight line, along a line parallel to the straight line wherein the transducers are arranged.

Hence, for each angular position of the transducer array, the plane oriented in the ultrasonic beam transmission direction and parallel to the line wherein the adjacent transducers are arranged is scanned.

This process is repeated for each of the predetermined angular positions of the transducer array, whereby a succession of scan planes is obtained which covers the whole extension of the object volume, as shown in FIG. 1. Essentially, each scan plane consists of a set of lines of view along which the transmitted ultrasonic beam is focused at a certain depth or distance from the surface of the transducers, the focusing rule remaining the same for each line of view.

It will be understood that the swing axle is set back from the transmission plane of the transducers 20, which allows to maintain a substantially identical distance between the transducers and the facing wall of the covering cap 30.

Figure 5:
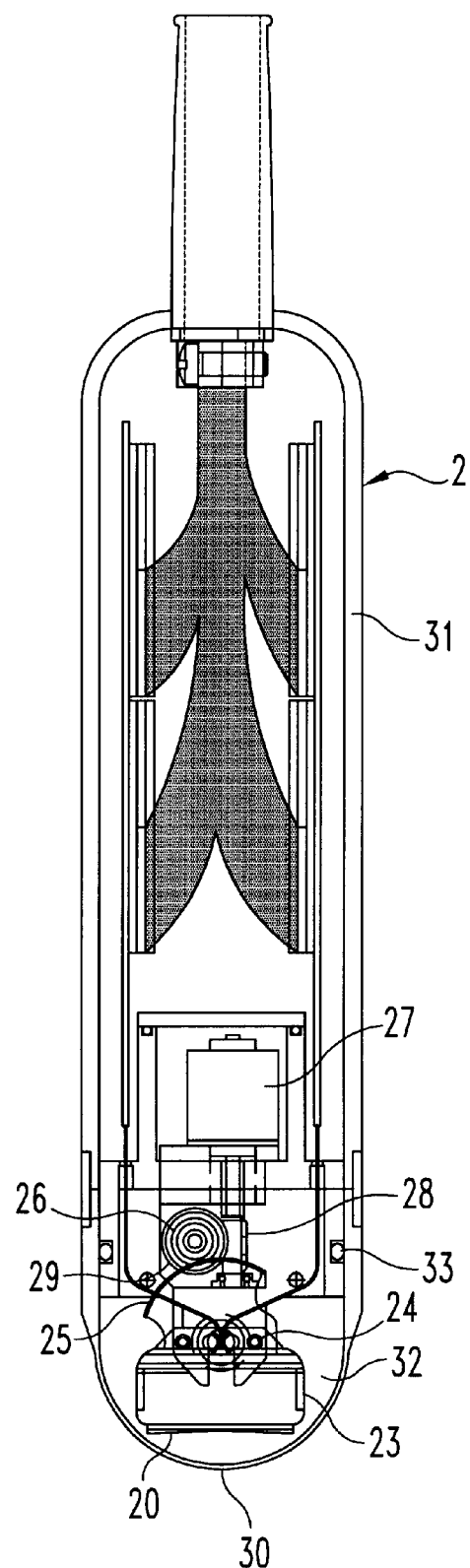
FIGS. 5 and 6 are two sectional views like those of FIGS. 3 and 4 of a probe of the phased array-sector type.
Figure 6:
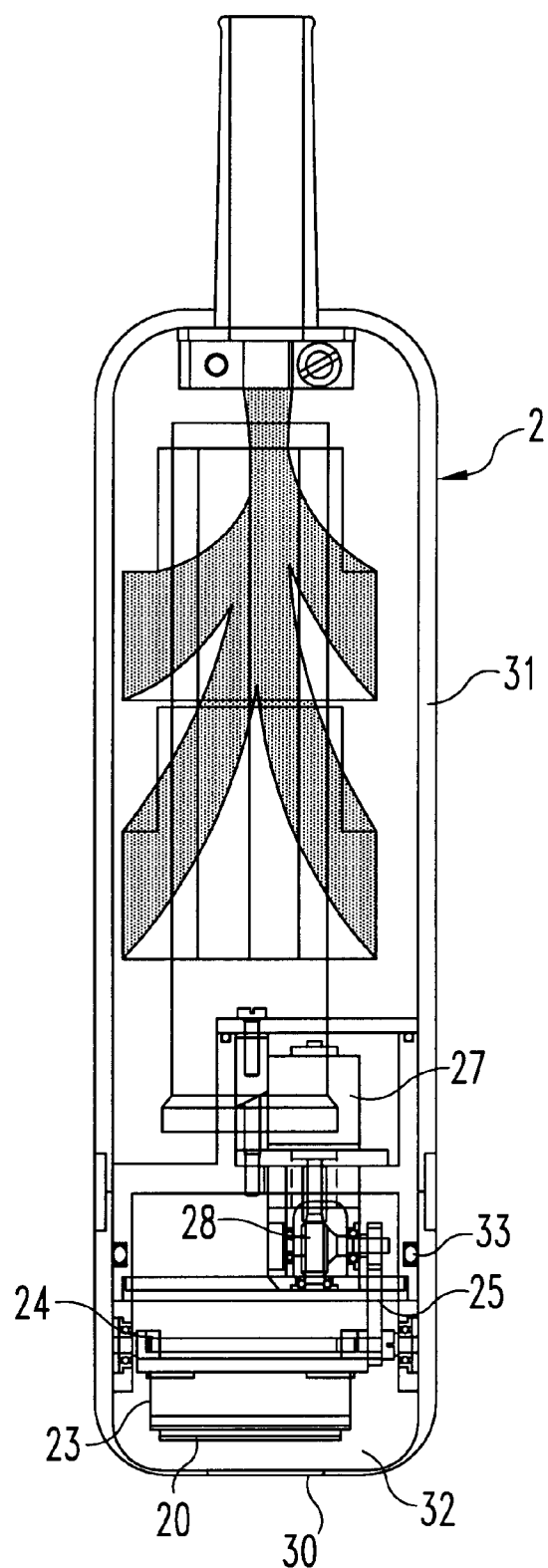

The probe as shown in FIGS. 5 and 6 has a construction which is substantially similar to the above described probe of FIGS. 3 and 4. However, in this case, the transducer is a phased-array transducer, differing in that the focusing rule varies according to the line of view.

The transducer array 20 according to the two preceding embodiments may be linear, as described above, or two-dimensional, i.e. having transducers arranged in two directions, i.e. over a surface. In this case, a section slice of the object volume may be scanned instead of a section plane. This does not change the operation of the apparatus and the steps of the method according to the present invention which, though being described with specific reference to probes having a linear transducer array, may also apply to probes with two-dimensional transducers, by simply modifying the scanning and processing control rule, based on the fact that information to be obtained has to relate not only to several scan planes but to several scanning slices, or three-dimensional scanning sections.

Figure 7:
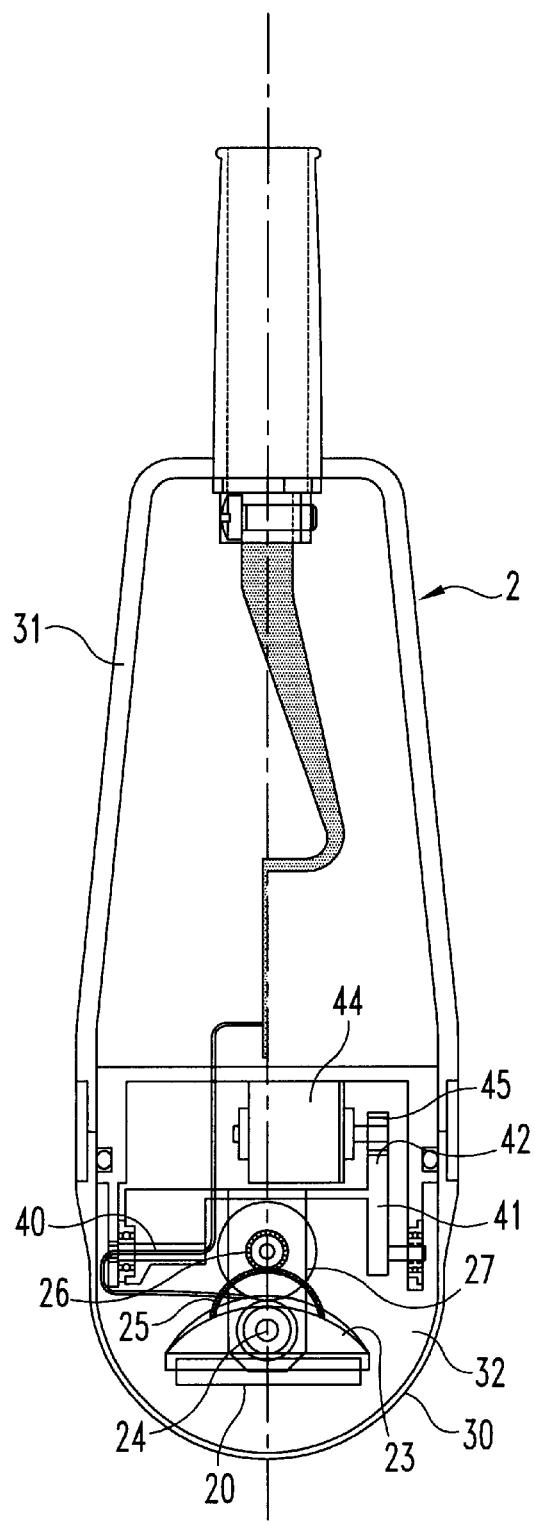
FIGS. 7 and 8 are two sectional views like those of the preceding figures of a probe of the phased array-sector type.
Figure 8:
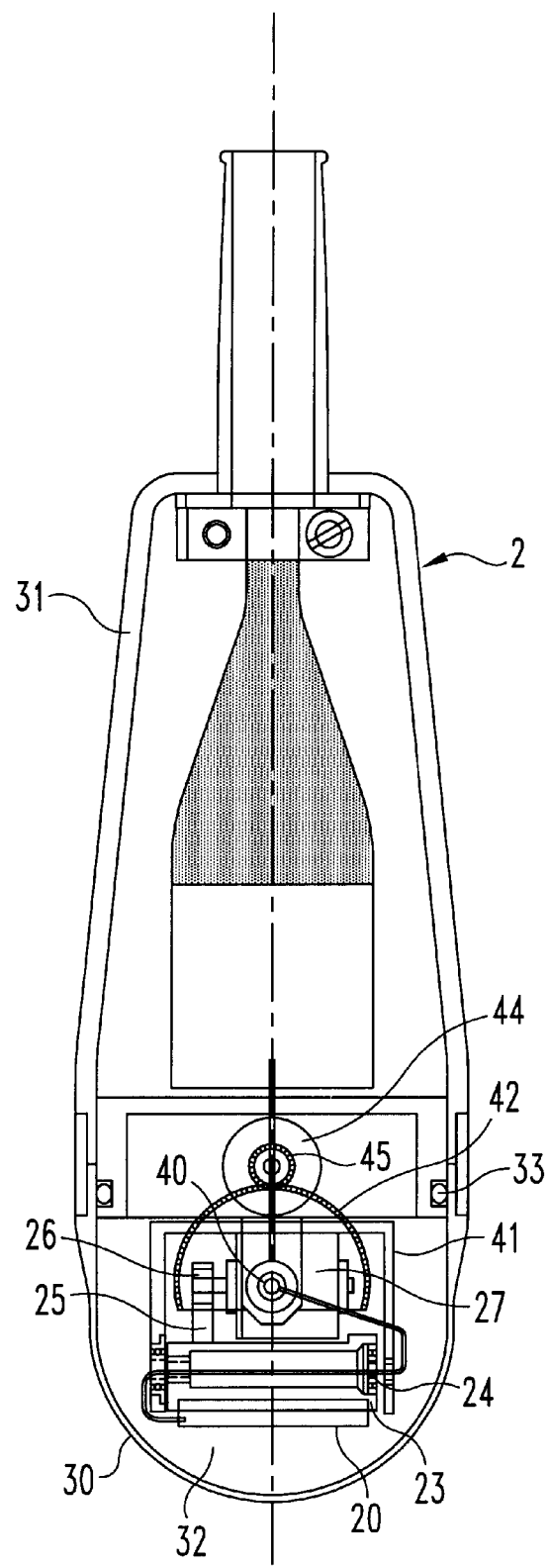

The probe as shown in FIGS. 7 and 8 is an additional embodiment of the above described probes. In this probe, the transducer array 20 swings about the axis of a first axle parallel to the extension of the adjacently arranged transducers by means of the same mechanism as previously described with reference to the probes of FIGS. 3 to 6. However, the transducer is mounted in such a manner as to additionally swing about the axis of another axle 40, perpendicular to the first swing axle and parallel to the plane containing said first swing axle. This arrangement allows to scan a section plane by swinging the transducer array about the axis of the second swing axle and this allows to use annular or mono transducers.

Obviously, the transducer array may also have a two-dimensional transducer arrangement, i.e. disposed over a surface, as described above for the probes of FIGS. 3 to 6.

In this probe, the transducer array 20, the support 23 swinging about the axis of first axle 24 parallel to the extension of the scan planes, the supports of said swing axle 24, the toothed circular section 25 integral with the transducer array support 23, the pinion 261 cooperating therewith, as well as the first stepper motor 27, are mounted on a support stirrup 41 which is supported so as to oscillate about the axis of the axle 40. The stirrup 41 is integral, on the side diametrically opposite to the axle 40, and like the mechanism allowing oscillation about the axle 24, with a circular rack 42 which is engaged with a driving pinion 45, rotatably driven by a second motor 44.

Unlike the above embodiments, the two motors 27 and 44 cooperate directly with the circular racks 25, 42, with no drive intervening therebetween.

In this case, as stated above, the scan control processor has to control two motors 27 and 44 in a synchronized manner.

However, this embodiment provides an increased flexibility in handling imaging modes, as it allows to handle the combinations of swinging steps in the two directions in a simple and specific manner, so as to define arrays of scan planes whose orientations may differ from those imposed by linear probes, or by probes with a two-dimensional transducer arrangement only swinging about one axis.

The probe according to this embodiment may be easily used, by an appropriate focusing rule, variable with the inclinations of the two axles 24 and 40, to perform targeted scans of a few lines of view only, without having to scan whole volumes.

Theoretically, the two above probes might as well perform a similar targeted and selective scan, but, besides the electronic control for management of the focusing rule, the rule for sweeping the lines of view which form the scan plane should also be changed electronically, whereas, in the probe of FIGS. 7 and 8, the control is limited to the simple physical oscillation of the transducer array.

When a two-dimensional transducer array is used, the probe of FIGS. 7 and 8 allows to scan individual unit volumes of the object volume.

An advantage of the probes according to the three different described embodiments, when combined with a transducer array having a side-by-side arrangement in two spatial directions, i.e. over a surface, is that it allows to obtain so-called three-dimensional transducer arrays, which can perform a three-dimensional scan only electronically, by varying the transducer activation rule, and/or by varying the focusing rule, ensuring, with a limited number and extension of transducers, the whole object volume is covered.

In fact, the oscillation of the transducer array ensures that the probe is swept to scan the whole object volume, which would require very large two-dimensional transducer arrays. In this case, transducers may be still provided in small numbers, and the small scanning extension in the direction of the size of the two-dimensional transducer array is obviated by the oscillation of the transducer array in said direction. The arrangement to provide small numbers of transducers in the probe is important, since each transducer must be connected by a dedicated wire. Therefore, in prior art probes having two-dimensional transducer arrays with a great number of transducers, a great number of connecting wires are required, which makes the probe difficult or complex to manufacture, particularly when a small size of the probe is desired, to ensure access even in restricted space conditions, whereas in the probe of the invention, the smaller number of transducers eliminates or reduces both probe connection and size problems.

Particular advantages are provided by the double mechanical oscillation probe as shown in FIGS. 7 and 8. In this case, the transducers arranged in two directions may be provided in very small numbers, with reference to the extension of the transducer array in both directions. The oscillation in the two transverse, particularly perpendicular directions allows to obviate the restriction of the probe effectiveness range. The arrangement of this embodiment also provides a probe, whose transducers are arranged on a plane, i.e. in two dimensions, which has a very small size, at least as regards the probe head.

This type of probe is well adapted to the use for imaging volumes or organs whose windows of view have very small sizes, such as for intercostal imaging, or the like.

Obviously, the invention is not limited to what is described and illustrated herein, but may be greatly varied especially as regards construction without departure from the inventive principle disclosed above and claimed below. In particular, the invention may be used in combination of any kind of imaging mode or method known in the art, with or without the use of contrast agents or the like.

What is claimed is:

1. A method of ultrasound imaging, including the following steps:

transmitting ultrasonic beams generated by transducers into an object volume corresponding to an object body or a part thereof;

receiving and storing signals generated by the ultrasonic beams in said object volume;

processing the received signals into image data associated to image dots or lines of a video display;

displaying at least a few image data on the display in accordance with parameters set by a user and related to a predetermined section or projection plane of the image of said object volume, processing of ultrasonic beams and/or displaying being specifically predetermined with reference to a preliminary selection of a section plane or an image projection plane of the object volume to be imaged, characterized in that it includes the following additional steps:

defining a virtual volume coincident with the object body or part thereof or a three-dimensional reference system, provided it has a definite orientation with respect to the imaging planes generated by said transducer;

selecting the section plane of the object body and/or part thereof along which ultrasound imaging is to be performed;

determining the position-defining coordinates for the dots which form said section plane along which imaging is to be performed, with the reference to the virtual volume;

restricting scanning operation to the region which coincides with said section plane along which imaging is to be performed;

transmitting the transmission signals and receiving the reflected echoes only along such lines of view of the probe which coincide with the surface or the projection slice of the selected section plane along which imaging is to be performed;

only processing and displaying the received echo signals.

2. A method as claimed in claim 1, characterized in that it is provided in combination with so-called three-dimensional ultrasound imaging.

3. A method as claimed in claim 1, characterized in that it is provided in combination with the injection of contrast agents into the object volume and with the detection of echo signals having harmonic frequencies of the second and/or higher order than the fundamental frequency.

4. A method as claimed in claim 1, characterized in that ultrasound scanning of the whole object volume is performed by receiving and storing reflected echo signals even of regions which are not coincident with the selected section plane or with the selected projection plane to be imaged while there is provided, simultaneously to or after image processing of signals coinciding with said planes, even processing of the remaining signals or signal portions into image data, there being provided different ultrasonic signal transmission and reception modes along the different scan lines which form each scan plane of the probe depending on whether the lines are coincident with the section plane to be imaged or non coincident therewith.

5. A method as claimed in claim 4, characterized in that scanning is performed with non optimal parameters, hence in a shorter time, for the scan lines which do not coincide with the section plane along which imaging is to be performed, whereas scan parameters are optimized for the scan lines which coincide with the section plane along which imaging is to be performed.

6. A method as claimed in claim 4, characterized in that the number of scan lines is reduced or a smaller number of transducers is activated to scan along the scan lines which do not coincide with the scan plane to be imaged, as compared with the number of lines or the number of transducers activated in the regions of the scan plane of the probe which coincide with the section plane along which imaging is to be performed.

7. A method as claimed in claim 1, including the following steps:
   performing a three-dimensional scan of the object volume by transmitting ultrasonic signals into the object body while focusing them along individual section planes having different orientations or positions and such that all the individual section planes together cover different and predetermined sections arranged over the extension of the whole object volume, or focused on individual adjacent unit volumes which cover, as a whole, all the object volume, and receiving the corresponding reflected echoes, each section plane being formed by a series of parallel and adjacent section lines, or each section slice being formed by a plurality of unit scan volumes, which are formed, in turn, by a plurality of adjacent scan lines;
   processing the received echo signals into image data in relation to their position in space with reference to scan modes;
   storing image data in a memory in univocal relation to the corresponding spatial position information and transforming them into image dots or lines on a video display;
   the method being further characterized by the following steps:
      generating a virtual volume, containing or coinciding at least partly with the volume of the object body or part thereof or a three-dimensional reference system, provided it has a precise orientation with respect to the imaging planes generated by the ultrasound probe;
      setting or selected the orientation of a predetermined section plane of the object volume or of a predetermined projection plane of said object volume prior to the scanning, processing and displaying process;
      determining the lines of said selected section or projection plane which intersect the individual scan planes and/or the unit volumes coinciding with said section or scan plane;
      only transmitting ultrasonic signals and receiving echoes therefrom along said lines of said selected section or projection plane which intersect the individual scan planes and/or the unit volumes coinciding with said section or scan plane;
      processing into image data and into signals for controlling the video display only such reflected signals or parts thereof which are related to said lines intersecting the selected section plane or projection plane to be displayed.

8. A method as claimed in claim 1, characterized in that it includes the following steps: defining a virtual volume, which at least partially coincides with or encloses the object body or part thereof or a three-dimensional reference system, with respect to a first scan plane of the ultrasound probe;
   selecting and setting position and orientation parameters of the section plane or of the projection plane to be imaged, relative to said virtual volume;
   identifying the transmission signals and the corresponding echoes which relate to dots, unit volumes, lines or discrete bands or slices coincident or substantially coincident with said section plane or with said projection plane to be imaged by simply comparing the position references of the dots and/or lines contained in said section plane or in said projection plane to be imaged with the scan planes of the probe;
   three-dimensionally scanning the object volume only in the region coinciding with the section plane along which imaging is to be performed, and storing the received echo signals and spatial position references univocally related thereto, with reference to individual discrete dots or unit volumes and/or to discrete scanning liens or bands or slices;
   relating position and orientation parameters for the section plane or projection plane which has been predetermined for imaging with the references to the spatial position of each received signal;
   only processing the received echo signals relating to dots or lines which coincide or substantially coincide with the dots or lines contained in the section plane or in the projection plane to be displayed.

9. A method as claimed in claim 1, characterized in that it may be arranged that only certain ultrasonic signals are transmitted and/or that focusing is performed only in certain regions or along certain lines, with reference to the lines or volumes of each scan plane and/or scan unit volume respectively, which intersect with said selected section plane or projection plane.

10. A method as claimed in claim 1, characterized in that, in order to ensure a certain reliability, scanning tolerances may be set to provide that scanning is not only performed along lines or unit volumes coinciding with the section plane along which imaging is to be performed or with the projection thereof, but also, within predetermined limits, in the regions directly adjacent to said section plane or to the projection thereof.

11. A method as claimed in claim 1, characterized in that it is provided in combination with scanning probes of the so-called linear electronic or mechanical or phased array type, or with so called sector—sector probes or with probes of the above or different type having transducers arranged over a two-dimensional surface, named 2D array probes.

12. A method as claimed in claim 1, characterized in that it provides that probes are displaced in a direction substantially transverse to the scan planes or to scan volumes in a manual, mechanical, or motorized manner, by linear indexing or by oscillation or rotation, the relative position of the individual planes being determined with reference to a reference plane and by means of position sensors which detect the position and the orientation of the probe or, in the case of motorized means, thanks to the prefixed steps of the probe from the starting position to scan the first scan plane.

13. A method as claimed in claim 1, wherein all received signals related to the whole volume scan are stored and processed off line and are stored in appropriate physical or electronic mass-memory units to be possibly recalled by the operating personnel to display, at a later time, images of any section or projection plane or images obtained from the combination of said images.

14. An ultrasound imaging apparatus, particularly for three-dimensional ultrasound imaging, according to the method as claimed in claim 1 comprising:
 a probe having transducers for generating ultrasonic pulses and receiving said pulses;
 a control unit for generating and focusing said transmitted ultrasonic pulses in accordance with predefined scan modes;
 a unit for reconstructing reflected echo signals with reference to focusing modes;
 a unit for converting echo signals received and reconstructed into image data and a unit for storing said image data in which said image data are related to position parameters based on scan modes;
 a unit for processing said image data into signals for controlling a displaying monitor;
 a unit for setting spatial orientation parameters of the section and projection planes of the object volume along which imaging is to be performed;
 a unit for controlling access to said image data and processing of said data into control signals for the displaying monitor based on the settings of spatial orientation parameters of section or projection planes of the object volume to be displayed;
 said control unit for controlling access to said image data and processing of said data into control signals for the displaying monitor being controlled based on the settings of spatial orientation parameters of section or projection planes of the object volume to be imaged for transmission and reception, as well as for processing and storage of such signals which only relate to dots, lines or unit volumes coinciding with said selected section or projection planes along which imaging is to be performed.

15. An apparatus as claimed in claim 14, characterized in that it includes a main processor whereto the means for inputting the selected orientation of the plane to be imaged and the selected ultrasound imaging modes are associated, which controls a scan control processor whereto the scanning probe is connected, a processor for converting image data into monitor control signals and a storage control processor, whereto means for storage onto physical media are connected; a RAM unit whereto the positions of the individual scanning dots, planes or unit volumes are provided by the scan processor and whereto the storage control processor and the processor for converting scans into image data, as well as the displaying monitor are connected.

16. An apparatus as claimed in claim 14, characterized in that the RAM unit is a four input/output memory.

17. An apparatus as claimed in claim 16, characterized in that the RAM unit includes inputs/outputs for data and addresses, the addresses being intended to univocally define the spatial positions of image data being univocally related thereto.

18. An apparatus as claimed in claim 16, characterized in that the probe is connected, by its echo signal output to the dedicated data input of the RAM unit whereas the scan control processor is connected to the dedicated address input of the RAM unit, and the scan converting processor, the so-called scan converter is connected to a dedicated input/output and to the dedicated address input of said memory.

19. An apparatus as claimed in claim 16, characterized in that the scan converting processor is a so-called linear or two-dimensional converter.

20. An apparatus as claimed in claim 16, characterized in that the displaying monitor is connected to a dedicated data input/output and to a dedicated address input/output of the RAM unit.

21. An apparatus as claimed in claim 16, characterized in that the storage control processor is connected to a dedicated data input/output and to a dedicated address input/output.

22. An apparatus as claimed in claim 14, characterized in that it provides the use of probes for three-dimensional imaging, particularly linear motorized probes of the electronic or mechanical type and/or of the so-called phased array type.

23. An apparatus as claimed in claim 22, characterized in that the probe case includes a housing in an end portion thereof, which is sealed and houses the transducer array, the swing axle, and the drive, and a housing for accommodating and allowing the passage of the connecting wires and of the motor, the two housing being separated from each other in a liquid-tight manner and there being provided a liquid-tight passage for the connecting wires and the motor shaft from one housing to the other.

24. An apparatus as claimed in claim 22, characterized in that the probe is of the mechanical type, the transducer array being allowed to swing along two transverse axles.

25. An apparatus as claimed in claim 24, characterized in that the two swing axles are parallel to the plane which is in turn parallel to the transmission surface of the transducer array.

26. An apparatus as claimed in claim 24, characterized in that each of the swinging movements along one of the two axles respectively is controlled by a separate motor through a drive.

27. An apparatus as claimed in claim 24, characterized in that the probe has a member for supporting the transducer array which is mounted in such a manner as to swing about one of the two axes of the swing axles and which support is connected, through a mechanical drive to a first control motor, said support member, together with the transducer array, said first swing axle and their control motor being supported on a second support member which is in turn mounted in such a manner as to swing about the axis of a second swing axle transverse to the other and there being provided drive means to mechanically connect the second support member to a second control motor.

28. An apparatus as claimed in claim 24, characterized in that the transducer array is not disposed along a straight line, but over a surface, thereby being named two-dimensional array.

29. An apparatus as claimed in claim 14, characterized in that the probe comprises an array of transducers arranged side-by-side along a straight line and supported in such a manner as to swing about the axis of an axle parallel to said straight line along which the transducer array extends, there being provided an electric motor which controls the oscillation of the transducer array through a drive.

30. An apparatus as claimed in claim 29, characterized in that the electric motor and the drive for starting the oscillation of the transducer array are housed inside a probe case.

31. An ultrasound imaging probe, particularly for three-dimensional imaging, characterized in that it comprises an array of transducers arranged side-by-side along a straight line transverse to the longitudinal axis of said probe and supported in such a manner as to swing about the axis of an axle parallel to said straight line along which the transducer array extends, there being provided an electric motor which controls the oscillation of the transducer array through a drive.

32. A probe as claimed in claim 31, characterized in that the electric motor and the drive for starting the oscillation of the transducer array are housed inside a probe case.

33. A probe as claimed in claim 31, characterized in that the probe case includes a housing in an end portion thereof, which is sealed and houses the transducer array, the swing axle, and the drive, and a housing for accommodating and allowing the passage of the connecting wires and of the motor axle, the two housings being separated from each other in a liquid-tight manner and there being provided with a liquid-tight passage for the connecting wires and the motor axle from one housing to the other.

34. An apparatus as claimed in claim 31, characterized in that the probe is of the mechanical type, the transducer array being allowed to swing along two transverse axles.

35. An apparatus as claimed in claim 34, or characterized in that the two swing axles are parallel to the plane which is in turn parallel to the transmission surface of the transducer array.

36. A probe as claimed in claim 29 or 31, characterized in that each of the swinging movements along one of the two axles respectively is controlled by a separate motor through a drive.

37. A probe as claimed in claim 31, characterized in that the probe has a member for supporting the transducer array which is mounted in such a manner as to swing about one of the two axes of the swing axles and which support is connected, through a mechanical drive to a first control motor, said support member, together with the transducer array, said first swing axle and their control motor being supported on a second support member which is in turn mounted in such a manner as to swing about the axis of a second swing axle transverse to the other and there being provided drive means to mechanically connect the second support member to a second control motor.

38. A probe as claimed in claim 31, characterized in that the transducer array is not disposed along a straight line, but over a surface, thereby being named two-dimensional array.

* * * * *